United States Patent [19]

Tuy et al.

[11] Patent Number: 4,712,178
[45] Date of Patent: Dec. 8, 1987

[54] MALFUNCTIONING COMPUTED TOMOGRAPHY DETECTOR CORRECTION METHOD

[75] Inventors: Heang K. Tuy, Cleveland; Narasimharao Koka, Richmond Heights, both of Ohio

[73] Assignee: Picker International Inc., Highland Heights, Ohio

[21] Appl. No.: 13,159

[22] Filed: Feb. 10, 1987

Related U.S. Application Data

[63] Continuation of Ser. No. 675,623, Nov. 28, 1984, abandoned.

[51] Int. Cl.⁴ .................................................. A61B 6/02
[52] U.S. Cl. ........................................ 364/414; 378/901
[58] Field of Search ................... 364/414; 378/901, 19, 378/4, 14, 11, 99; 250/366, 367

[56] References Cited

U.S. PATENT DOCUMENTS

| | | | |
|---|---|---|---|
| 4,091,416 | 5/1978 | Riethmuller et al. | 364/414 |
| 4,136,388 | 1/1979 | Lindqust | 364/414 |
| 4,178,510 | 12/1979 | Wagner | 364/414 |
| 4,437,161 | 3/1984 | Anderson | 364/414 |
| 4,549,265 | 10/1985 | Deckers et al. | 364/414 |
| 4,559,557 | 12/1985 | Keyes et al. | 364/414 |

Primary Examiner—Jerry Smith
Assistant Examiner—Kimthanh Tbui
Attorney, Agent, or Firm—Watts, Hoffmann, Fisher & Heinke Co.

[57] ABSTRACT

A method for approximating X-ray detector data from malfunctioning computed tomography detectors. A view of data is gathered for each of a plurality of detectors in a stationary detector scanner. Data for each malfunctioning detectors is approximated by interpolating data from detectors closely positioned with respect to the malfunctioning detectors after regions of high contrast within a cross-section of interest have been identified.

14 Claims, 6 Drawing Figures

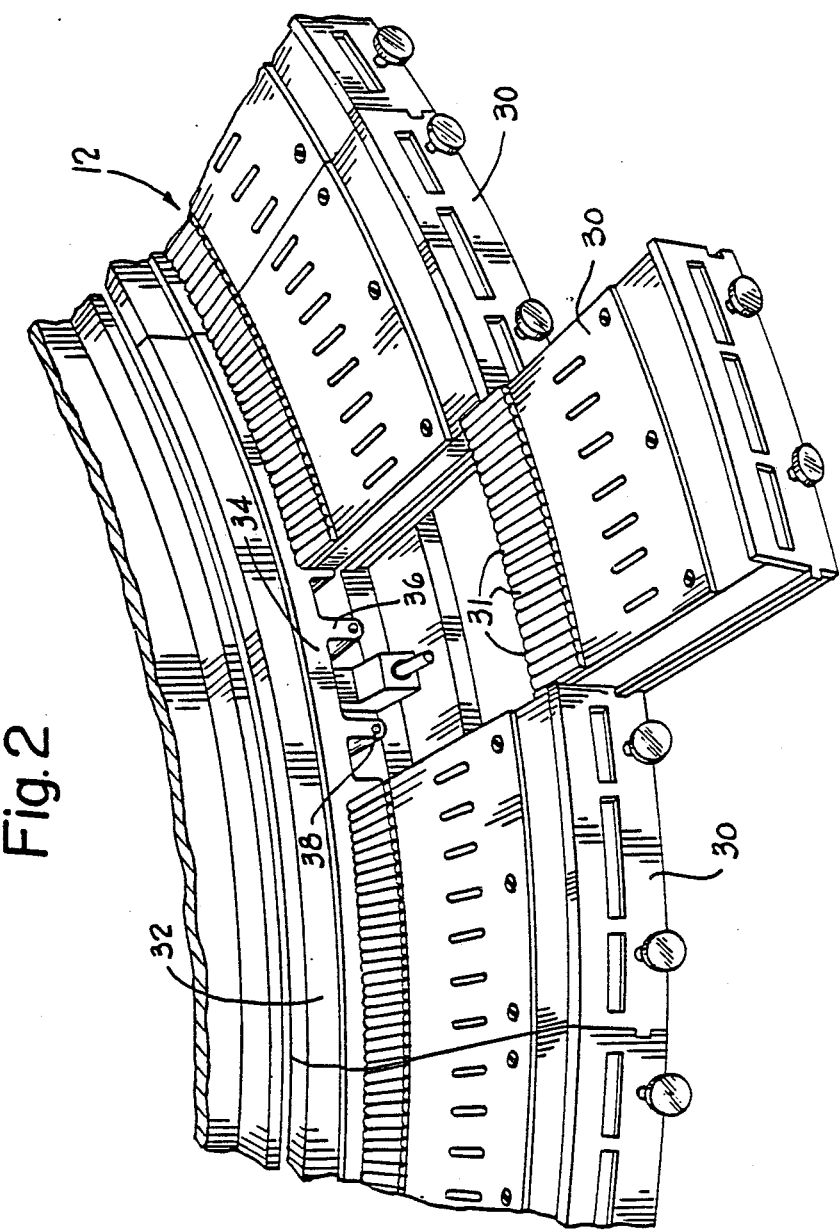

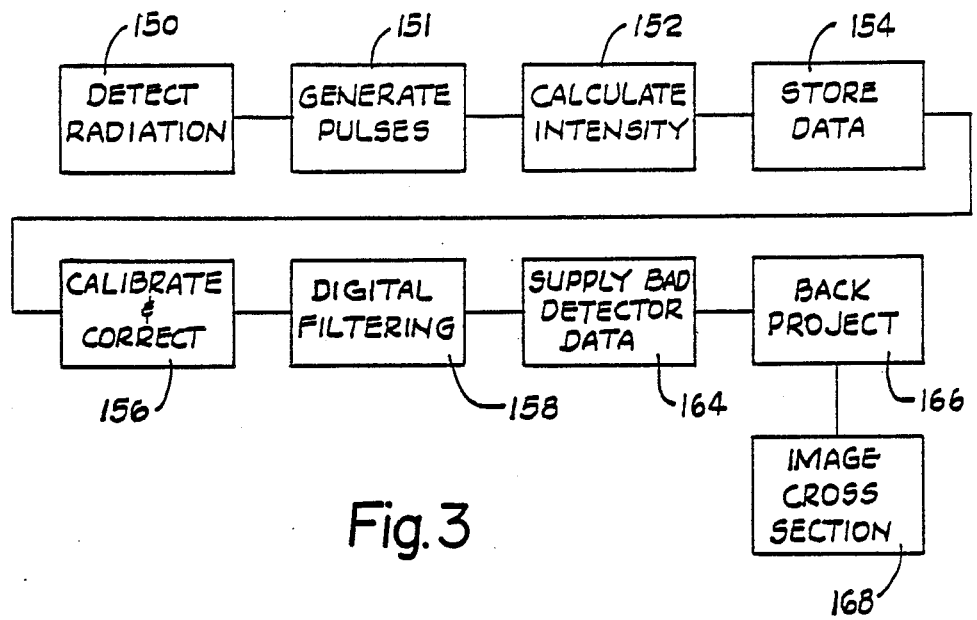
Fig. 3
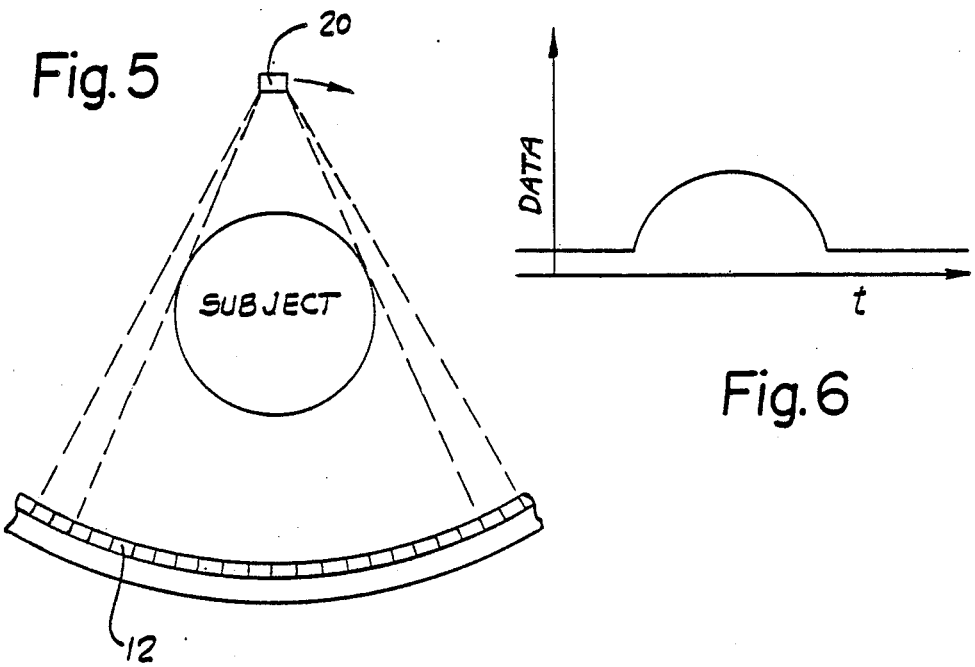
Fig. 5
Fig. 6

MALFUNCTIONING COMPUTED TOMOGRAPHY DETECTOR CORRECTION METHOD

This is a continuation of co-pending application Ser. No. 675,623 filed on Nov. 28, 1984 and now abandoned.

DESCRIPTION

TECHNICAL FIELD

The present invention relates to computed tomography and more particularly to a method for attributing radiation intensity readings to malfunctioning X-ray detectors based upon the intensity readings of closely adjacent functioning detectors.

BACKGROUND ART

One feature common to all computed tomography systems is that they must include apparatus for detecting radiation intensity variations indicative of a patient's internal structure. In a first generation CT system this apparatus involved a single detector which moved in unison with a moving X-ray source. Second and third generation CT systems included a plurality of detectors also moving with respect to the patient and in a fourth generation system a high number of detectors are fixed with respect to a patient.

Early computed tomography systems used one of two types of X-radiation detectors. One type detector is the scintillation detector which uses a crystal for converting X-radiation impinging upon it into visible light which is detected by a photomultiplier tube. This tube converted the light into an electrical current and amplified this current to a level suitable for measuring the radiation intensity.

Gas ionization chambers are also used in some CT designs. In such a chamber the high energy radiation passing from the source through the patient to the detector causes an ionization of the gas stored in the ionization chamber. The current generated in this ionization process, gives an indication of X-radiation intensity.

Photodiode solid state detectors have increasingly replaced the photomultiplier tube techniques for detecting light from a scintillation crystal. Detectors now typically comprise a scintillation crystal mounted in close proximity to a photodiode which produces an output current proportional to the X-ray intensity striking the scintillation crystal.

In a fourth generation CT design an array of 600 or more closely packed photodiodes are positioned in a circular array to circumscribe a patient aperture. X-radiation from a rotating X-ray tube impinges upon each detector in the array as the X-ray tube orbits around the patient. Electronics coupled to each detector convert the current output from the detector photodiode into a digital signal proportional to the X-ray intensity impinging upon a given detector.

The solid state detectors have advantages over gas ionization or photomultiplier tube detectors. Perhaps the most significant advantage the solid state detectors have is the very close packing density these detectors permit in a fourth generation machine. A typical scintillation crystal and photodiode is mounted in a package sufficiently small to allow well over 1000 detectors to be positioned in a reasonable space for scanning.

In a CT apparatus requiring in excess of 1000 detectors mounted in a circular array about a subject aperture, it is possible that certain detectors may malfunction and no longer produce meaningful intensity data. It is also possible that the electronic circuitry for analyzing the output from the detectors will also, on occasion, malfunction to the point where the output from the circuitry may be inaccurate or unreliable. In either event, it is desirable that the view resulting from the bad detector or circuit (detector channel) is corrected prior to reconstruction.

In the past when a detector or circuit has malfunctioned, an intensity reading has been assigned to the malfunctioning detector by averaging the intensity outputs from the two detectors closely adjacent to the malfunctioning detector. Experience with this simple averaging technique indicates that it is not a full solution since using a simple averaging on occasions leads to artifacts in the reconstructed picture. These artifacts typically comprise streaks across the reconstructed image which correspond to no internal structure in the subject. These streakings or artifacts occur because incorrect values are assigned to the sample in the averaging technique.

A more sophisticated technique for supplying intensity readings to malfunctioning detectors and/or circuits is disclosed in pending U.S. patent application Ser. No. 441,857 entitled "Method and Apparatus for Computed Tomography Imaging" to DeMeester et al which was filed in the U.S. Patent Office on Nov. 15, 1982, now abandoned.

The DeMeester et al invention selectively chooses an interpolation based upon differences in intensity readings from closely adjacent functioning detectors. This technique can still, however, produce artifacts under certain conditions. In particular high attenuation intensity samples corresponding to a high contrast region within a cross-section can result in an inappropriate choice of interpolation data.

DISCLOSURE OF INVENTION

In accordance with the invention, specific processing is performed to isolate intensity readings from high contrast regions of a cross-section in a computed tomography scan. These intensity readings are specially treated to avoid an inappropriate choice in assigning interpolated data for malfunctioning detectors in those regions of high contrast. Testing of the disclosed invention shows reduction in artifacts when imaging high contrast regions.

The invention has utility in a computed tomography scanner which includes a number of spaced radiation detectors. As a first step, malfunctioning detectors within the multitude of detectors are identified so that an approximating technique can be performed for those malfunctioning detectors. For each group of one or more malfunctioning detectors sample readings from a functioning detector closely adjacent the group are examined to identify a reading corresponding to a high contrast region within a scanning cross-section.

Once this intensity reading is identified, intensity readings from a second functioning detector adjoining the group of one or more malfunctioning detectors are analyzed to identify a second high contrast reading. Intensity information is then supplied for malfunctioning detector groups by interpolating the high contrast readings over a region of intensity samples for the malfunctioning group of one or more detectors. Once data has been supplied to the malfunctioning detector groups this data in combination with actual data taken during a computed tomography scan is used to reconstruct an image of the subject.

In a preferred technique, the first high contrast intensity reading is obtained by sequentially comparing each sample reading in a so-called view to determine if that sample reading is attenuated below a threshold value. If the threshold has been exceeded, this intensity reading corresponds to a region of high contrast in the patient and the boundary of this high contrast is identified by taking gradients in the vicinity of the high attenuation reading. This two-step process of first identifying a threshold value and then taking gradients in the region of that value results in the choice of one or more high attenuation points for the samples of the particular detector view.

Once this has been accomplished a corresponding detector reading is needed from an opposite side of the malfunctioning group. This is accomplished by scanning the intensity readings in close proximity to the already chosen first intensity reading for a region of maximum attenuation. Then a series of gradients are taken to find a border of this contrast region to identify the second intensity reading.

Now that two intensity readings are identified, these two readings define a gradient direction along which interpolation is to proceed. For detectors spaced about the two detectors which define the gradient a number of interpolations are performed to supply the missing data for the one or more malfunctioning detectors within the group.

For those detector readings which do not exceed the threshold values, the aforementioned DeMeester et al technique is utilized to supply missing detector radiation readings. Once all detector samples have been approximated by one or the other of the interpolation processes this data in conjunction with data from functioning detectors is utilized in reconstructing a cross-sectional image. Techniques for providing these reconstructions are well known within the computed tomography art.

From the above it should be appreciated that one object of the invention is a new and improved technique for supplying missing detector radiation intensity readings to enable a computed tomography image to be reconstructed even though some detectors are malfunctioning. This and other objects and advantages of the invention will become better understood when a detailed description of a preferred embodiment of the invention is described in conjunction with the accompanying drawings.

BRIEF DESCRIPTION OF THE DRAWINGS

FIG. 2 is a schematic perspective view of a portion of a stationary detector array used by the FIG. 1 scanner to detect radiation intensity from a moving X-ray source;

FIG. 3 is a flow chart showing steps in a computed tomography reconstruction process;

FIGS. 5 and 6 depict variations in X-ray transmission with X-ray source movement for an individual detector in the detector array.

BEST MODE FOR CARRYING OUT THE INVENTION

Figure 1:
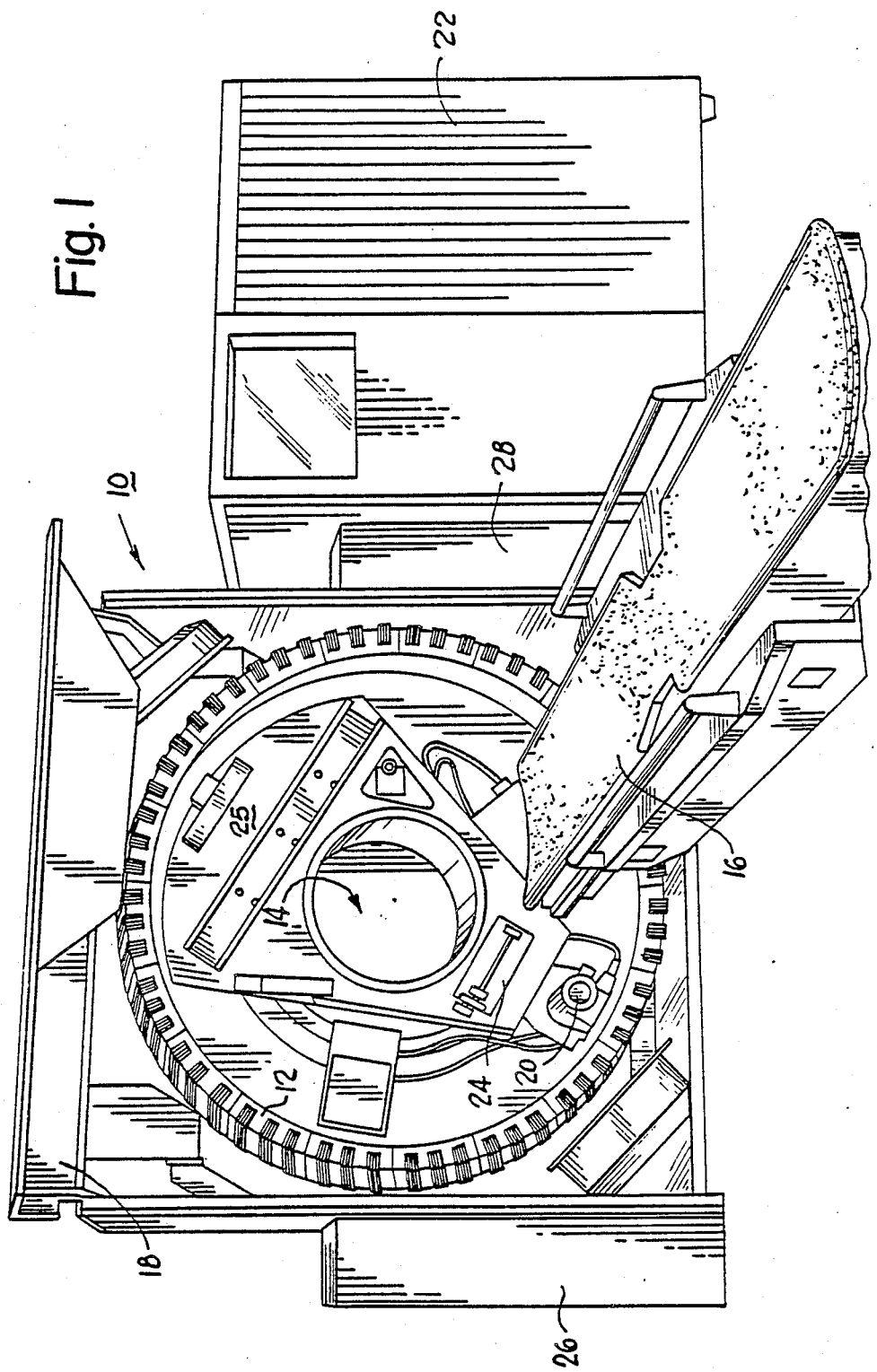
FIG. 1 is a schematic perspective view of a computed tomography scanner.

Turning now to the drawings, FIG. 1 illustrates a computed tomography scanner 10 used in imaging cross-sectional slices of interest in a patient. The scanner 10 is a fourth generation computed tomography scanner where a fixed array 12 of detectors surrounds a patient aperture 14. During imaging a patient is positioned on a couch 16 and then moved into and through the patient aperture 14 until a cross-sectional slice to be imaged is appropriately positioned. A scanner front panel 18 is hinged to the scanner housing. Two panel portions swing away from their closed position to allow the interior of the scanner 10 to be accessed. The scanner housing is supported by a pair of supports 26, 28 and can be tilted about an axis extending through the supports parallel to the floor. In this way, patient cross-sections other than a vertical cross-section can be obtained without repositioning the patient.

The generation of X-radiation requires a series of electronic subsystems to energize an X-ray source. In an X-ray tube, highly accelerated electrons are directed to a tube anode from a cathode and in particular electrons having nearly 150,000 electron volts of energy strike the anode to produce X-radiation.

In computed tomography scanning, special electronics needed to analyze intensity values as detected by the array 12 are also required. This specialized electronics counts output pulses from the scanner detectors as well as controls movement of an X-ray tube and coordinates this movement with the analysis of the output signals.

High speed computed tomography scanning is possible only through use of a high speed data processing computer 22. A presently preferred computer is a 32 bit Perkin-Elmer mini-computer with a disc storage capacity of 320 million bytes. This computer performs the sophisticated data processing for reconstructing a grid-like mapping of density variations inside the patient slice from intensity readings taken from the detector array surrounding the patient aperture. The particular computer chosen is responsible for not only analyzing and reconstructing cross-sectional image densities but also for displaying this information on a console (not shown).

When the front panel is opened a fixed array 12 of X-radiation detectors is visible (see FIG. 2). The illustrated array 12 completely encircles the patient aperture 14. During scanning, the x-ray tube 20 generates an X-ray beam which is shaped by a collimator 24 to provide a generally planar spread beam of radiation that passes through the aperture to opposed detectors in the array 12. The X-radiation is attenuated by the patient (or any other objects in the path of the x-radiation) and its intensity is then detected by detectors in the array 12. The tube 20 and a collimator 24 are both mounted to a CT frame 26 which is rotatably mounted to the scanner 10. A motor (not shown) imparts rotational motion to the frame 25 which is journalled on stationary portions of the scanner 12 by a bearing (not shown) which surrounds the patient aperture.

The array 12 of detectors is made up of individual modules 30 (FIG. 2) which each support a plurality of closely spaced detectors 31 in fixed relation around patient aperture 14. In accordance with a preferred design, each module 30 supports sixty detectors so that the 20 modules comprising the array 12 supports 1200 detectors in a circular array.

Each of the modules 30 can be easily mounted to or removed from the scanner 10 to facilitate assembly or maintenance of an assembled unit. A stationary gantry 32 supports a number of module mounts 34, with each module mount defining a series of fingers 36 which extend radially outward from the module mount. These fingers define threaded openings 38 into which threaded connectors on the modules are screwed to mount the modules about the patient aperture. During assembly, a first module is screwed into place and other modules 30 comprising the detector array 12 are successively mounted to a module mount 34 in coacting relationship with the first module until an entire array of twenty modules has been positioned in place.

Each detector 31 comprises a scintillation crystal coupled to a photodiode which in turn is mounted to a ceramic mounting block. The detector is encapsulated in an aluminum can which reflects visible light while allowing X-radiation to be freely transmitted to the scintillation crystal. In operation, the X-radiation from the X-ray tube impinges upon the scintillation crystal which converts the X-radiation to visible light which in turn affects the current flow in the photodiode. Changes in current produced by the X-radiation are converted from an analog current signal into a sequence of pulses which are counted.

Electronics for generating these pulses in response to current changes in the photodiode are known in the art. The pulses are then counted and divided by the time period in which they are counted to obtain an indication of the intensity of the X-radiation impinging upon the detector at a given time. Circuitry for performing this counting function is disclosed in U.S. Pat. No. 4,052,620 to Brunnett which is assigned to the assignee of the present invention. That prior patent is incorporated herein by reference.

The steps of detecting the radiation 150 and generating the pulses 151 as well as determining the intensity 152 are depicted in a flow chart (FIG. 3) schematically describing the computed tomography process. These three steps 150, 151, 152 are followed by taking the logarithm of the data and a storing 154 of that data in the computer. The X-ray intensity measured by a detector is inversely proportional to the exponential of the line integral of the density of the subject for a given radiation path. The logarithm of the intensity data yields density data rather than attenuation information.

The remaining steps in the computed tomography process are performed by the computer 22. The computer first performs a series of calibration and correction calculations 156 on the data. These calculations are based upon data obtained during a CT set-up phase. These calculations take into account variations in detector sensitivity, gain, and offsets in the electronics. Once these calibration steps have been completed, a digital filtering step 158 is performed where all data from each detector is filtered in accordance with one of a number of techniques known in the art. Two known techniques employ convolution or fast fourier transforming (FFT) of data. In the latter case the process consists of performing a forward FFT of the data, multiplying the transformed data by a spacial frequency filter and then performing an inverse fast fourier transform to produce the filtered data.

At a next stage of the computed tomography process, those detectors which are malfunctioning are assigned filtered data 164 based upon the filtered data from those detectors which are supplying valid data. Finally, all data, both from those detectors that are functioning and those which are not, are back projected 166 into a memory to produce an image of a particular patient slice under examination. Once this back projection process has been completed, this data is again stored and utilized in imaging 168 a picture of this slice on a viewing console.

If the subject inside the patient aperture 14 were generally uniform in density, that portion of the radiation which misses the subject is essentially unattenuated and the X-radiation passing through the thickest part of the subject will be attenuated to the greatest extent.

Shown in FIG. 6 is a plot of the data stored in the computer for a given detector as that detector senses radiation from the source 40 in its orbital path about the cross-section subject shown in FIG. 5. As the source 20 rotates about the subject initially, no attenuation in radiation occurs and the corresponding data values for a particular detector will be a minimum. As the X-radiation source continues to move, the radiation striking the detector of interest will begin to be attenuated by the subject and the corresponding data values stored in the computer will begin to increase until the radiation impinging upon that detector undergoes maximum attenuation at which point the data will peak at a maximum value. As the source 20 continues to move, the attenuation will be less as the radiation passes through a smaller cross-section until the radiation again passes unattenuated from the source 20 to the detector of interest.

The entire data array for a period a detector is irradiated by the source 20 is known as a view. The views from each of the detectors comprising the detector array 12, are stored on the computer's disc storage system prior to the digital filtering of that data. In accordance with a preferred design, each detector view comprises 1,024 data samples, each of which must be digitally filtered, and then back projected across a grid or mapping of the cross-section of interest.

The samples listed in Table 1 represent filtered data values from five adjacent detectors in the array 12. Since a particular view for a detector comprises 1,024 of these points, it is appreciated that only a very limited portion (8 samples) of the view is shown in Table 1. Consecutive samples depict intensity readings from one detector at successive time intervals during a scan. The samples from different detectors in a given column are intensity readings at closely related yet not identical times.

TABLE 1

|    | 1 | 2 | 3 | 4 | 5 | 6 | 7 | 8 |
|----|---|---|---|---|---|---|---|---|
| −2 | $S_1$ | $S_2$ | $S_3$ | $S_4$ | $S_5$ | $S_6$ | $S_7$ | $S_8$ |
| −1 | $S_1$ | $S_2$ | $S_3$ | $S_4$ | $S_5$ | $S_6$ | $S_7$ | $S_8$ |
|  0 | $S_1$ | $S_2$ | $S_3$ | $S_4$ | $S_5$ | $S_6$ | $S_7$ | $S_8$ |
| +1 | $S_1$ | $S_2$ | $S_3$ | $S_4$ | $S_5$ | $S_6$ | $S_7$ | $S_8$ |
| −2 | $S_1$ | $S_2$ | $S_3$ | $S_4$ | $S_5$ | $S_6$ | $S_7$ | $S_8$ |

Various techniques are known for determining which detectors have malfunctioned. One procedure is to perform a calibration scan and view the back projected results of that scan. Streaks or artifacts pointing radially away from a single point at the edge of the picture are a strong indication that a detector (or its associated circuitry) has malfunctioned. This suspicion can be confirmed by testing the detector output directly. Another technique is to display the data from a sequence of detectors on the console and look for variations which should not exist. This is possible, for example, when the scanner is running a test scan on air or water and there should be only small variations in the detector output around the array 20.

Once it is known which detectors have gone "bad" missing data for those detectors is assigned by the computer. The DeMeester et al bad detector correction is done according to a gradient scheme, the algorithm of which is now briefly explained. Consider detector '$D_0$' as a bad detector, and $D_{-1}$ and $D_{+1}$ are the good detectors adjacent to each side of detector $D_0$. Let $S_1, S_2 \ldots$ be the sampled values in each view. Abbreviate ($D_0$, $S_3$) as the sample $S_3$ of detector view $D_0$. Consider the correction for sample ($D_0$, $S_3$). Edge gradients are computed in the vertical, left and right directions according to the following equations:

| | |
|---|---|
| vertical gradient = | $\|(D_{-1}, S_3) - (D_{+1}, S_3)\|$, |
| left gradient = | $\|(D_{-1}, S_2) - (D_{+1}, S_4)\|$, |
| right gradient = | $\|(D_{-1}, S_4) - (D_{+1}, S_2)\|$. |

The minimum of the three gradients is chosen, and then the interpolation is done in the minimum gradient direction, to obtain the value for ($D_0$, $S_3$). This procedure is repeated for all the samples ($S_1, S_2 \ldots$ etc) of detector $D_0$.

Though the interpolation is done in the minimum gradient direction, sometimes this may lead to an unreasonable value for a corrected sample in a bad view. Consider detector $D_0$ as a bad detector, and $D_{-1}$ and $D_{+1}$ as the good detectors adjacent to each side of detector $D_0$.

| Detector | Samples | | | | |
|---|---|---|---|---|---|
| $D_{-1}$ | $H_1$ | $L_2$ | $L_3$ | ... | Here 'H' abbreviates high |
| $D_0$, | $L_1$ | $H_2$ | $L_3$ | ... | attenuation value and 'L' |
| $D_{+1}$ | $L_1$ | $L_2$ | $H_3$ | ... | low attenuation value. |

In computing the three gradients for sample ($D_0$, $H_2$) one gets:

| | |
|---|---|
| vertical gradient = | $\|(D_{-1}, L_2) - (D_{+1}, L_2)\|$, |
| left gradient = | $\|(D_{-1}, H_1) - (D_{+1}, H_3)\|$, |
| right gradient = | $\|(D_{-1}, L_3) - (D_{+1}, L_1)\|$. |

It is appropriate to replace the value ($D_0$, $H_2$) by interpolating in the left gradient direction since a high attenuation value will be derived from two corresponding high attenuation values of the adjacent views. If the minimum of the three gradients is chosen, however, this can be other than the left gradient. This is because usually the difference between two corresponding higher attenuation values is larger than the difference between two lower attenuation values.

It has been noticed that streaks in the image produced by the DeMeester et al bad detector correction are due to the improper values assigned to the higher attenuation samples of a bad detector view. Correctly identifying those samples corresponding to a high contrast object and appropriately assigning sample data in the region of this object is accomplished by the computer in accordance with the FIG. 4 flow chart.

As a first step in the FIG. 4 routine a determination is made concerning which detectors or detector channels are improperly functioning and they are identified for the computer for later access.

At a second step each detector from the bad detector list is accessed and the computer determines how many consecutive detectors including this designated detector are bad. This number is given the designation "M".

The computer then scans (step 3) the sample data from two good views adjoining the bad detector or detectors and stores these two good view samples into storage buffers.

At step 4 of the process the computer scans sample data from one of the good views for high attenuation samples corresponding to a high contrast object. In performing this step the computer considers two consecutive samples starting from the first sample of a given detector view. If either of the samples has a value less than a certain threshold value (MVAL) the computer goes to the next sample. If both samples have a value higher than the threshold, a gradient is calculated between the two samples. If this gradient value is less than a certain threshold, the computer goes on to the next sample. If the gradient is larger than the threshold value the computer has found a high attenuation value corresponding to a high contrast object.

At step 5 of the process the computer scans neighboring samples in the vicinity of the maximum gradient found in step 4 checking for the absolute maximum gradient between any two samples. The sample with maximum attenuation contributing to this maximum gradient is designated "IX".

The sample "IX" of the first view analyzed during steps 4 and 5 is chosen (step 6) as the center of a window of samples for checking for a maximum gradient in the second good view. Thus in Table 1 if sample $S_3$ was found to be a region of maximum gradient for functioning detector $D-1$ about bad detector $D_0$, this sample would be a centering point for a window "X" detectors wide for functioning detector $D+1$ in determining a maximum gradient for detector $D+1$. In the following discussion this second detector sample (maximum attenuation) is given a designation "IY".

Figure 4:
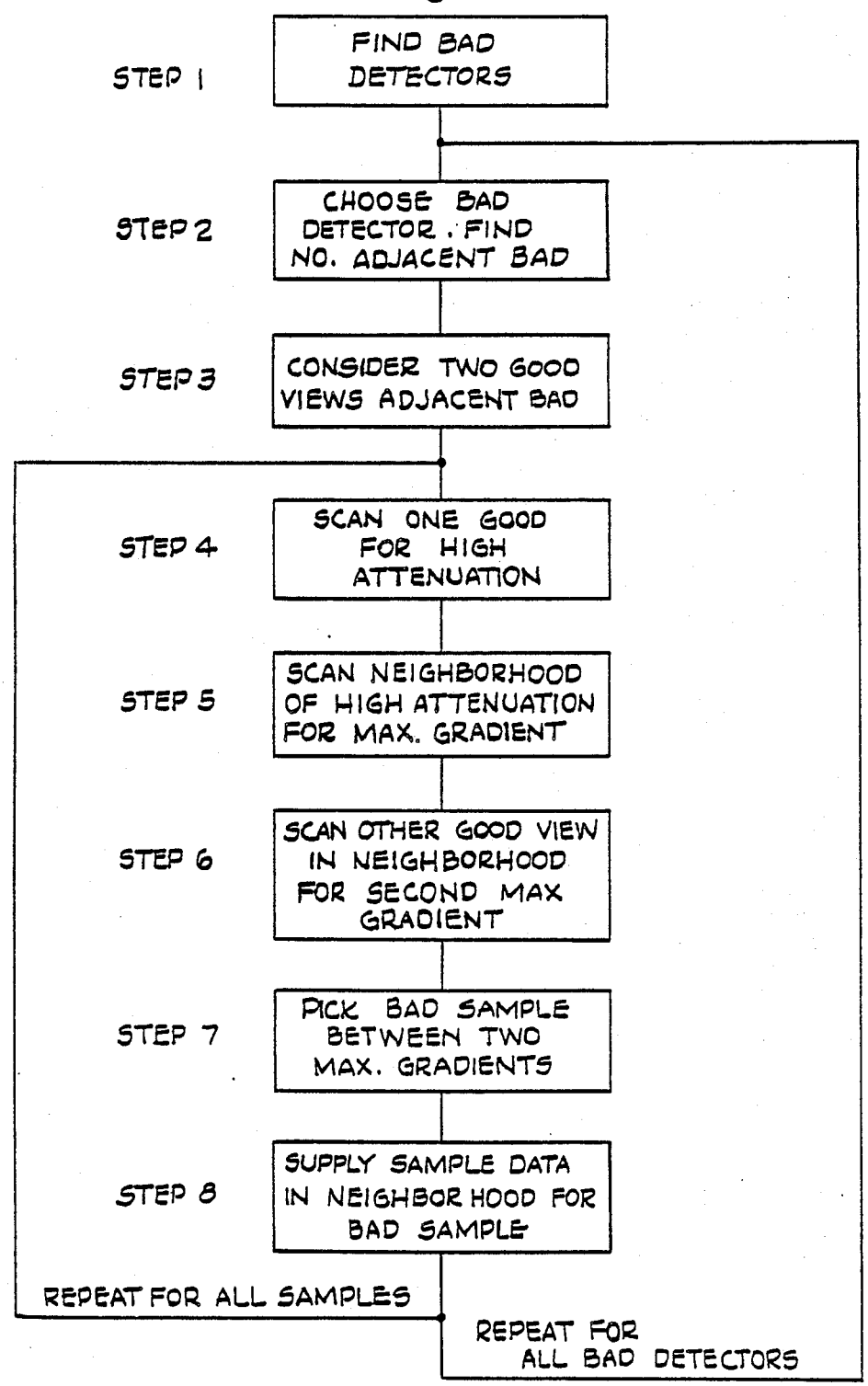
FIG. 4 is a flow chart of a method for approximating intensity data for malfunctioning detectors in the FIG. 2 array.

Step 7 of FIG. 4 depicts a step of choosing which malfunctioning detector samples are to be supplied data. If G1 and G2 are good detectors on each side of the one or more bad detectors, let M be the number of bad detectors present between G1 and G2. Designate $IZ_1$, $IZ_2, \ldots IZ_M$ as the sample number in the bad views ($B_1$, $B_2 \ldots B_M$) at which it is assumed that a maximum gradient occurs. The value of each maximum gradient sample is calculated as follows for each bad view.

$$IZ_I = [1 - (I/M+1)] \cdot IX + [I/M+1] \cdot IY \quad (1)$$

Where $IZ_I$ represents the sample number at which the maximum gradient occurs for bad views $B_1, B_2 \ldots B_M$, when $I = 1, 2, \ldots M$ respectively. If only one bad detector is present between views G1 and G2, equation (1) simplifies to:

$$IZ = (IX + IY)/2 \quad (2)$$

Once the sample number ($IZ_I$) is found corresponding to a bad detector view, at step 8 attenuation values of the samples in the neighborhood of ($IZ_I$) are calculated by interpolating the samples of the two good views on each side of the bad views, in the neighborhood of (IX) and (IY). The interpolation is done according to equation 3 below:

$$VAL_{(IZ_I)} = [1-(I/M+1)]*VAL_{(IX)} + [I/M+1]*VAL_{(IY)} \quad (3)$$

where $VAL_{(IZ_I)}$ is the attenuation value of sample $IZ_I$, $VAL_{(IX)}$ is the attenuation value of sample IX, and $VAL_{(IY)}$ is the attenuation value of sample IY. If only one bad detector is present between the views G1 and G2, the above equation simplifies to:

$$VAL_{(IZ)} = VAL_{(IX)} + VAL_{(IY)})/2 \quad (4)$$

A window of samples in the region of "IX" and "IY" are considered, and corresponding samples of each bad view $B_1, B_2, \ldots B_M$ in a parallelogram bounded by the endmost good detector samples are computed according to equation 3. Each sample pertaining to the window of samples considered in each bad view is calculated from its corresponding sample value in view G1 (top good view) and in view G2 (bottom good view). For example the values at $IZ_1, IZ_2, \ldots IZ_M$ of views $B_1, B_2, \ldots B_M$ which lie on the line joining IX and IY, are computed from the attenuation values at samples IX and IY of view G1 and G2. Similarly the samples of views $B_1, B_2, \ldots B_M$ which lie on a line drawn parallel to the line joining samples IX and IY are computed from the samples of views G1 and G2, which lie on the same line. This process is repeated until all the samples of views $B_1, B_2, \ldots B_M$ are obtained.

Steps 4 through 8 are repeated for all the samples in view G1, to find all the high attenuation samples corresponding to all high contrast objects in the view. Steps 2 through 8 are repeated for all consecutive bad detectors existing in the data area.

The procedure documented in FIG. 4 calculates sample intensity data corresponding to a high contrast object. The DeMeester et al correction process is used to obtain other sample data for a bad view in those regions not identified at step 4 in FIG. 4.

Once data has been generated for all bad or malfunctioning detectors, the data is used to reconstruct an image. The FIG. 4 flow chart defines a program written in FORTRAN for use on the Perkin-Elmer computer. The disclosed invention could be implemented on other computers with other computer languages and it is the intent that the invention include all modifications and alterations from the disclosed implementation falling within the spirit or scope of the appended claims.

What is claimed is:

1. In a computed tomography scanner of a type where multiple closely spaced radiation detectors detect radiation intensity at multiple times during a subject study, a method for reconstruction imaging comprising the steps of:
   identifying malfunctioning detector groups with each such group being comprised of one detector or a plurality of adjacent detectors;
   examining consecutive sensed intensity readings from a first functioning detector closely positioned in relation to a first group of one or more malfunctioning detectors to identify a first high contrast reading corresponding to a high contrast region within a scanning subject;
   examining consecutive sensed intensity readings from a second functioning detector separated from the first functioning detector by said first group of one or more malfunctioning detectors to indentify a second high contrast reading corresponding to said high contrast region;
   interpolating said first and second high contrast readings to obtain one or more interpolated intensity readings corresponding to one or more malfunctioning detectors; supplying said one or more interpolated intensity readings to said one or more malfunctioning detectors; and attributing said interpolated intensity readings to the one or more malfunctioning detectors in the first malfunctioning detector group to approximate data which would have been sensed by said one or more malfunctioning detectors;
   repeating the examining and supplying steps for each of said malfunctioning detector groups; and
   using both sensed intensity readings from functioning detectors and interpolated intensity readings for malfunctioning detector groups to reconstruct an image of said subject.

2. The method of claim 1 where the examining step for each of said first and second functioning detectors is accomplished by identifying a high attenuation reading from said first and second functioning detectors and identifying a maximum difference in readings in a range of readings near said identified high attenuation reading.

3. In a compound tomography scanner of a type where multiple closely spaced radiation detectors detect radiation intensity at different times, a method for reconstruction imaging of a patient cross section comprising the steps of:
   identifying groups of malfunctioning detectors with each such group being comprised of one detector or a plurality of adjacent detectors;
   examining a first set of sensed intensity readings from a first functioning detector closely positioned in relation to one group of malfunctioning detectors to identify a first high contrast reading corresponding to a high contrast region within a scanning cross-section;
   examining a second set of sensed intensity readings from a second functioning detector closely psitioned in relation to said one group of malfunctioning detectors to identify a second high contrast reading;
   interpolating said first and second high contrast intensity readings to obtain one or more interpolated intensity readings corresponding to one or more malfunctioning detectors; supplying said one or more interpolated intensity readings to said one or more malfunctioning detectors; and attributing said interpolated intensity readings to the one malfunctioning detector group;
   repeating said examining steps for other groups of malfunctioning detectors;
   supplying interpolated intensity readings to other groups of malfunctioning detectors, and
   using both sensed intensity readings from functioning detectors and interpolated intensity readings for malfunctioning detector groups to reconstruct an image of said cross-section.

4. The method of claim 3 where the examining step for each first functioning detector is accomplished by identifying a high attenuation reading from said first functioning detector and identifying a maximum difference between readings from said first functioning detector taken during time before and after said high attenuation reading.

5. The method of claim 4 wherein said second high contrast reading is determined by selecting a high attenuation reading contributing to a maximum difference in readings in a time interval approximately the same as a time interval said first high contrast reading is obtained.

6. A method for reconstruction imaging for a subject cross-section with a computed tomography scanner having multiple closely spaced detectors for obtaining sensed radiation intensity readings comprising the steps of:
- identifying groups of malfunctioning detectors with each such group being comprised of one detector or a plurality of adjacent detectors;
- examining sensed sample intensity readings from a first functioning detector closely positioned in relation to a first group of malfunctioning detectors to identify a first high contrast reading corresponding to a high contrast region within a scanning cross-section;
- examining a second set of sensed intensity readings from a second functioning detector separated from said first functioning detector by said first group of one or more malfunctioning detectors to identify a second high contrast reading corresponding to the high contrast region;
- supplying intensity information to said malfunctioning detectors by interpolating said first and second high contrast readings to produce an interpolated reading for each malfunctioning detector of said first group;
- repeating the examining and supplying steps for all groups of malfunctioning detectors to supply one or more interpolated readings, and
- using both sensed readings from functioning detectors and interpolated readings for malfunctioning detector groups to reconstruct an image of said subject cross-section.

7. The method of claim 6 wherein multiple interpolations are each performed to supply multiple interpolated readings for each detector in the malfunctioning detector groups.

8. In a computed tomography scanner of a type where multiple closely spaced radiation detectors detect radiation intensity at multiple times during a subject study, said study defining a two dimensional mapping of intensity readings wherein each reading within said mapping is identified by a detector and sample number; a method for reconstruction imaging comprising the steps of:
- identifying malfunctioning detector groups with each such group being comprised of one detector or a plurality of adjacent detectors;
- examining consecutive sensed intensity readings from a first functioning detector closely positioned in relation to a first group of one or more malfunctioning detectors to identify a first high contrast reading corresponding to a high contrast region within a scanning subject;
- examining consecutive sensed intensity readings from a second functioning detector separated from the first functioning detector by said first group of one or more malfunctioning detectors to indentify a second high contrast reading corresponding to said high contrast region;
- interpolating between said first and second high contrast readings to obtain one or more interpolated intensity readings along a direction in said two dimensional mapping defined by said first and second high contrast readings corresponding to one or more malfunctioning detectors;
- supplying said one or more interpolated intensity readings to said one or more malfunctioning detectors; and attributing said interpolated intensity readings to the one or more malfunctioning detectors in the first malfunctioning detector group to approximate data which would have been sensed by said one or more malfunctioning detectors;
- repeating the examining and supplying steps for each of said malfunctioning detector groups; and
- using both sensed intensity readings from functioning detectors and interpolated intensity readings for malfunctioning detector groups to reconstruct an image of said subject.

9. In a compound tomography scanner of a type where multiple closely spaced radiation detectors detect radiation intensity at different times to define a two dimensional mapping of intensity readings wherein each intensity reading within said mapping is identified by a detector and a sample number; a method for reconstruction imaging of a patient cross section comprising the steps of:
- identifying groups of malfunctioning detectors with each such group being comprised of one detector or a plurality of adjacent detectors;
- examining a first set of sensed intensity readings from a first functioning detector closely positioned in relation to one group of malfunctioning detectors to identify a first high contrast reading corresponding to a high contrast region within a scanning cross-section;
- examining a second set of sensed intensity readings from a second functioning detector closely positioned in relation to said one group of malfunctioning detectors to identify a second high contrast reading;
- interpolating between said first and second high contrast intensity readings to obtain one or more interpolated intensity readings along a direction in said two dimensional mapping defined by said first and second high contrast readings corresponding to one or more malfunctioning detectors;
- supplying said one or more interpolated intensity readings to said one or more malfunction detectors; and attributing said interpolated intensity readings to the one malfunctioning detector group;
- repeating said examining steps for other groups of malfunctioning detectors;
- supplying interpolated intensity readings to other groups of malfunctioning detectors, and
- using both sensed intensity readings from functioning detectors and interpolated intensity readings for malfunctioning detector groups to reconstruct an image of said cross-section.

10. The method of claim 9 where the examining step for each first functioning detector is accomplished by identifying a high attenuation reading from said first functioning detector and identifying a maximum difference between readings from said first functioning detector taken during times before and after said high attenuation reading.

11. The method of claim 10 wherein said second high contrast reading is determined by selecting a high attenuation reading contributing to a maximum difference in readings in a time interval approximately the same as a time interval said first high contrast reading is obtained.

12. The method of claim 9 wherein additional interpolations are performed between other sensed intensity readings obtained by the first and second functioning detector along the direction defined by the first and second high contrast readings.

13. A method for reconstruction imaging of a subject cross-section with a computed tomography scanner having multiple closely spaced detectors for obtaining multiple sensed radiation intensity readings, said multiple detectors anmd sensed radiation intensity readings defining a two dimensional mapping of intensity readings wherein each intensity readings within the mapping is identified by a detector and a sample number; said method comprising the steps of:

identifying groups of malfunctioning detectors with each such group being comprised of one detector or a plurality of adjacent detectors;

examining sensed sample intensity readings from a first functioning detector closely positioned in relation to a first group of malfunctioning detectors to identify a first high contrast reading corresponding to a high contrast region within a scanning cross-section;

examining a second set of sensed intensity readings from a second functioning detector separated from said first functioning detector by said first group of one or more malfunctioning detectors to identify a second high contrast reading corresponding to the high contrast region;

supplying intensity information to said malfunctioning detectors by interpolating between said first and second high contrast readings along a direction in said two dimensional mapping defined by said first and second high contrast readings to produce an interpolated reading for each malfunctioning detector of said first group;

repeating the examining and supplying steps for all groups of malfunctioning detectors to supply one or more interpolated readings if a high contrast region is identified, and using both sensed readings from functioning detectors and interpolated readings for malfunctioning detector groups to reconstruct an image of said subject cross-section.

14. The method of claim 13 wherein multiple interpolations between sensed intensity readings from the first and second functioning detector are performed along the direction defined by the first and second high contrast readings to supply multiple interpolated readings for each detector in the malfunctioning detector group.

* * * * *